US010508305B2

(12) United States Patent
Nashtaali et al.

(10) Patent No.: US 10,508,305 B2
(45) Date of Patent: Dec. 17, 2019

(54) DNA SEQUENCING AND PROCESSING

(71) Applicants: Damoun Nashtaali, Tehran (IR); Seyed Abolfazl Motahari, Tehran (IR); Mehrdad Mehrbod, Tehran (IR); Babak Hossein Khalaj, Tehran (IR); Mazhareddin Taghivand, Campbell, CA (US)

(72) Inventors: Damoun Nashtaali, Tehran (IR); Seyed Abolfazl Motahari, Tehran (IR); Mehrdad Mehrbod, Tehran (IR); Babak Hossein Khalaj, Tehran (IR); Mazhareddin Taghivand, Campbell, CA (US)

( * ) Notice: Subject to any disclaimer, the term of this patent is extended or adjusted under 35 U.S.C. 154(b) by 198 days.

(21) Appl. No.: 15/442,864

(22) Filed: Feb. 27, 2017

(65) Prior Publication Data

US 2017/0166963 A1 Jun. 15, 2017

Related U.S. Application Data

(60) Provisional application No. 62/300,893, filed on Feb. 28, 2016.

(51) Int. Cl.
*C12Q 1/68* (2018.01)
*C12Q 1/6874* (2018.01)
*G16B 30/10* (2019.01)

(52) U.S. Cl.
CPC .......... *C12Q 1/6874* (2013.01); *G16B 30/10* (2019.02)

(58) Field of Classification Search
None
See application file for complete search history.

(56) References Cited

U.S. PATENT DOCUMENTS

| 5,502,773 | A | 3/1996 | Tibbetts et al. |
| 6,446,011 | B1 | 9/2002 | Floratos et al. |
| 2002/0010797 | A1 | 1/2002 | Moulton |
| 2006/0024716 | A1* | 2/2006 | Glover, III .......... C12Q 1/6816 435/6.1 |
| 2010/0137166 | A1* | 6/2010 | Kain ...................... C12Q 1/686 506/39 |
| 2011/0246084 | A1* | 10/2011 | Ronaghi ................. G06F 19/22 702/20 |

(Continued)

FOREIGN PATENT DOCUMENTS

WO 2016038220 A1 9/2015

OTHER PUBLICATIONS

Mark A Depristo et al., A framework for variation discovery and genotyping using next-generation DNA sequencing data, Nature GeNetics, May 2011, 491-498, vol. 43, No. 5.

*Primary Examiner* — Samuel C Woolwine
(74) *Attorney, Agent, or Firm* — Bajwa IP Law Firm; Haris Zaheer Bajwa

(57) ABSTRACT

An integrated system for sequencing a string of oligo-nucleotides is disclosed, the system includes a sequencer for sequencing a plurality of fragments of the string of oligo-nucleotides via identifying oligo-nucleotides of the fragments one by one and a processor for processing the identified oligo-nucleotides to determine the sequence of the string of oligo-nucleotides and to stop the sequencer from sequencing redundant fragments, where the sequencer and the processor operate in a cycle for each oligo-nucleotide of the fragments.

19 Claims, 16 Drawing Sheets

(56) References Cited

U.S. PATENT DOCUMENTS

| | | | | |
|---|---|---|---|---|
| 2013/0166221 A1* | 6/2013 | Inglis | ............ | G06F 19/22 |
| | | | | 702/20 |
| 2013/0260372 A1* | 10/2013 | Buermann | ......... | G01N 21/6428 |
| | | | | 435/6.1 |
| 2013/0274148 A1* | 10/2013 | Kain | ............ | C12Q 1/6837 |
| | | | | 506/38 |
| 2013/0331992 A1* | 12/2013 | Subramaniam | ......... | G06F 19/22 |
| | | | | 700/266 |
| 2015/0310165 A1* | 10/2015 | Mann | ............ | G06F 19/22 |
| | | | | 506/2 |
| 2015/0368638 A1* | 12/2015 | Steemers | ............ | C12Q 1/6869 |
| | | | | 506/4 |
| 2017/0228496 A1* | 8/2017 | Boutros | ............ | G06F 19/22 |

* cited by examiner

DNA SEQUENCING AND PROCESSING

CROSS REFERENCE TO RELATED APPLICATION

The present application claims priority from U.S. Provisional Patent Application Ser. No. 62/300,893, filed Feb. 28, 2016, entitled "DNA SEQUENCING AND PROCESSING METHOD: A UNIFIED APPROACH", which is incorporated herein by reference in its entirety.

TECHNICAL FIELD

The present disclosure generally relates to nucleic acids sequencing, particularly to systems and methods for synchronously sequencing and processing a string of oligo-nucleotides, and more particularly to integrated systems, methods and algorithms for synchronously sequencing and processing of a string of oligo-nucleotides.

BACKGROUND

Data generated from DNA sequencing machines are growing at an unprecedented rate. Extracting knowledge from this data is extremely tedious and usually requires very powerful computing machines. The main reason is that the volume of data generated for an experiment usually contains redundant data. Accordingly, extracting of useful information and removal redundant information becomes an important part of at the processing step. As an example, during the entire genome sequencing of Human genome with 100× coverage, each base, on average, presents 100 sequencing reads which means 99 percent of the data is redundant. Hence, there is a need for systems and methods to reduce the number of sequenced bases significantly in a sequencing process of a string of oligo-nucleotides, for example, a DNA sequencing process. Also, there is a need to decrease the generated data of read oligo-nucleotides to determine a nucleic acid sequence, for example, by avoiding reading and processing redundant or repetitive fragments.

SUMMARY

In one general aspect of the present disclosure an integrated system is described for sequencing a string of oligo-nucleotides. The system may include a sequencer for sequencing a plurality of fragments of the string of oligo-nucleotides via identifying oligo-nucleotides of the fragments one by one; and a processor for processing the identified oligo-nucleotides to determine the sequence of the string of oligo-nucleotides and to stop the sequencer from sequencing redundant fragments. The sequencer and the processor may operate in a cycle for each oligo-nucleotide of the fragments.

The above general aspect may include one or more of the following features. The oligo-nucleotides may be identified by using an identification technique that may be, for example, analyzing temperature signals, analyzing pH signals, or analyzing fluorescence photons of the oligo-nucleotides. The redundant fragments may include fragments having a threshold number of the same sequentially identified oligo-nucleotides with at least one other fragment.

According to an implementation, the processing of the identified oligo-nucleotides may include data analysis and a termination process. The data analysis may include analysis of the identified oligo-nucleotides of each fragment to determine the place of the fragment along the string of oligo-nucleotides and to determine the redundant fragments and the termination process may include sending a command to the sequencer to stop the sequencing of the redundant fragments.

According to an implementation, the data analysis may be assisted by an analysis process, for example quality analysis, alignment or genome assembly techniques. In an example, the data analysis may be done using an alignment method that may include aligning identified oligo-nucleotides of each fragment to a reference genome to determine the place of the fragment along the reference genome and to determine the redundant fragments.

According to an implementation, the termination process may be done by sending a terminating signal from the processor to the sequencer to remove the redundant fragments from further sequencing.

In another aspect of the present disclosure a method is described for sequencing a string of oligo-nucleotides. The method may include preparing a template including a substrate having a plurality of wells and a plurality of fragments from a string of oligo-nucleotides that may be attached within the wells; reading the oligo-nucleotides of the attached fragments; and processing the read oligo-nucleotides. The reading and the processing operations may be done in a cycle for each oligo-nucleotide of the fragments. Processing the read oligo-nucleotides may include mapping the read oligo-nucleotides along a genome; detecting redundant fragments; and sending a termination signal to stop the reading of the redundant fragments.

According to an implementation, the template may be prepared by shearing a number of the oligo-nucleotides string into a plurality of fragments; and attaching each fragment onto one well of the plurality of wells embedded on the substrate.

According to an implementation, reading the oligo-nucleotides of the fragments may include adding a solution of DNA polymerase and dNTPs to the substrate; and identifying one oligo-nucleotide of each fragment using an oligo-nucleotide identification technique. The oligo-nucleotide identification technique may include, for example, analyzing temperature signals, analyzing pH signals, or analyzing fluorescence photons of the oligo-nucleotides.

In an implementation, mapping of the read oligo-nucleotides along a genome may be done, for example, using an alignment method to align the read oligo-nucleotides of each fragment to a reference genome.

In an implementation, sending the termination signal may include applying a voltage to the bottom of the wells those are included the redundant fragments to achieve detaching the redundant fragments from the substrate.

DETAILED DESCRIPTION

After introduction of Sanger sequencing method in 1980 as the first generation of DNA sequencing, new technologies known as Next Generation of Sequencing (NGS) were gradually developed to achieve lower cost and higher throughput for extraction of genomic information.

NGS technologies consist of three main stages: template preparation, base calling and processing. In the template preparation stage, first, DNA fragments are randomly broken to small fragments, where such fragments are attached to solid surface of a template platform. After this step, two different approaches are traditionally used for preparing templates: (a) amplification of a single molecule and (b) single molecule preparation. The amplification of a single molecule is commonly adopted in many practical NGS methods, e.g., in Illumina machinery. However, in single molecule preparation methods, the time consuming amplification stage is discarded and sequencing is performed in real time on single molecules. Naturally, such approach relies on detection of single molecule signal which can be quite challenging in practice. After the template preparation stage, the observed signal must be detected for the base calling. The detected signal can be the temperature, pH, or the number of fluorescence photons. After detecting oligo-nucleotides, generated reads must be processed at the last stage. The processing stage may consist of alignment or fragment assembly schemes that can also exploit an existing reference genome. Downstream analysis for extraction of genomic information is subsequently executed after the processing stage. Accordingly, the template preparation and base calling stages are independent from the processing stage, thus the total length of all reads is sequenced and then processing is performed for all reads. Although the result leads to a tight bound, it is based on a tacit assumption that the set of reads is first collected through a sequencing process and then analyzed at the processing machine Incurrent DNA sequencing methods (e.g., one used by Illumina), a large amount of material is used for sequencing reads during a long period of time. These methods deal with a lot of generated data. The Lander-Watermans coverage bound shows that the total number of bases to be sequenced for the entire assembly of a genome with a length of G oligo-nuleotides, should be NL>GlogG, where N and L are number and length of the sequenced reads, respectively. Also, in the practical applications more than GlogG bases are involved and hence, the same order materials or resources must be used in the sequencing procedure. However, such result is based on the underlying assumption that sequencing and computing steps are performed independently.

Figure 1:
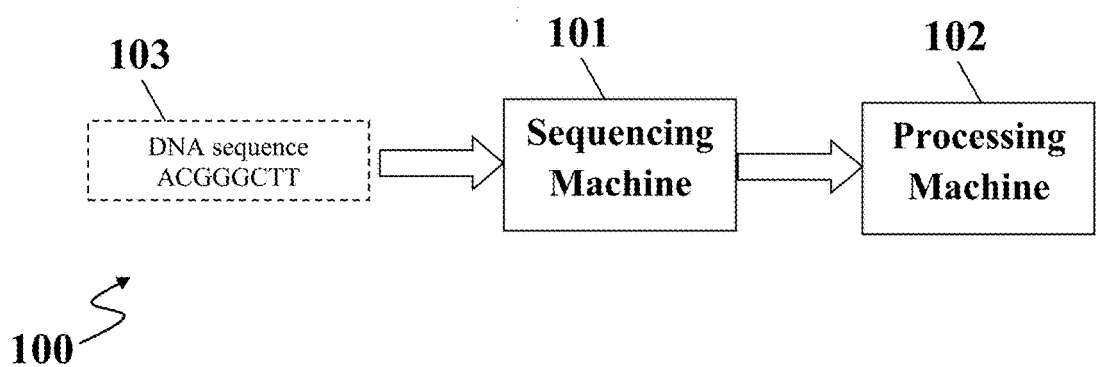
FIG. 1 illustrates a schematic of one exemplary embodiment of a classic system for sequencing a string of oligo-nucleotides.

FIG. 1A, illustrates a classic system 100 for DNA sequencing that may include a sequencing machine 101 for taking sample fragments from an exemplary genome 103 and sequencing as many reads as required to cover the entire genome 103; and a processing machine 102 for processing the reads to assemble the genome. The sequencing machine 101 and the processing machine 102 of the conventional system 100 work independently. First, all reads must be sequenced by the sequencer 101, then, a process is executed by the processor 102 on the output data to determine the sequence of an exemplary genome 103.

To overcome shortcomings of the conventional DNA sequencing methods and systems, for example, the problem described above, the present disclosure describes an exemplary system and an exemplary method to decrease the required time and resources/materials for sequencing a string of oligo-nucleotides, for example, sequencing DNA or RNA. Disclosed systems and methods are based on combining the sequencing and computing processes enabling one to re-sequence the entire genome with a smaller number of sequenced bases in total. Consequently, the disclosed systems and methods may reduce the cost of a DNA sequencing process via reducing time, materials or resource consumption and the required computational power.

The present disclosure describes systems and methods to reduce the computational power required to assemble a genome in a string of oligo-nucleotides sequencing processes. In an aspect, a processing unit may process the data on the fly and if the processing unit detects that the information from the remaining part of data is redundant it will stop further processing of that piece of data. Such early termination may have a significant effect on reducing computational complexity of the entire process. The disclosed systems and methods may control the depth of sequencing for obtaining the desired accuracy. Such control of the depth may be carried out by sequencing only informative bases and reducing over-read bases.

In an aspect, the present disclosure describes an integrated system for sequencing a string of oligo-nucleotides, for example DNA and RNA sequences. The system may include a sequencer and a processor, which may operate synchronously to determine a sequence of oligo-nucleotides.

Figure 2:
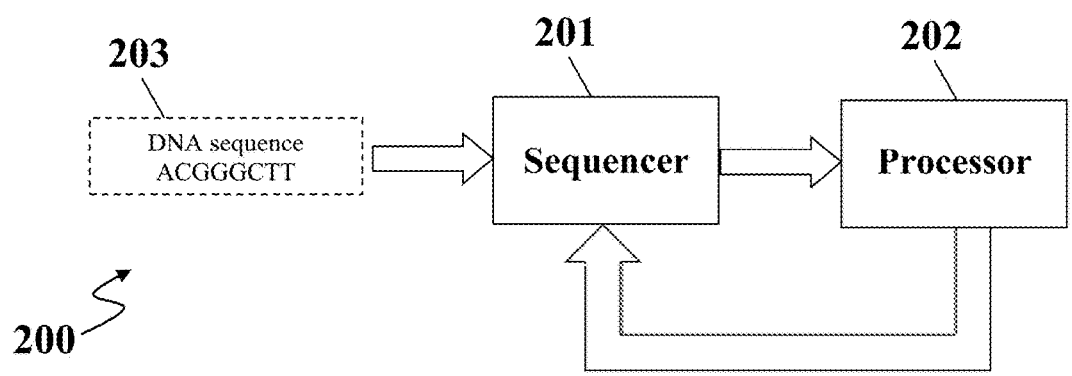
FIG. 2 illustrates a schematic of one exemplary embodiment of an integrated system for sequencing a string of oligo-nucleotides, according to exemplary implementations of the present disclosure.

FIG. 2 illustrates a schematic of one example of an integrated system 200 for sequencing a string of oligo-nucleotides, for example DNA and RNA including a number of oligo-nucleotide bases. Referring to FIG. 2, the exemplary system consistent with embodiments of the present disclosure may include a sequencer 201 that may be configured to sequence a plurality of fragments of the string of oligo-nucleotides 203 via identifying oligo-nucleotides of the fragments one by one; and a processor 202 that may be configured to process the identified oligo-nucleotides to determine the sequence of the string of oligo-nucleotides 203 and to stop the sequencer 201 from sequencing redundant fragments. The sequencer 201 and the processor 202 may operate in a cycle for each oligo-nucleotide of the fragments.

A "fragment" as used herein, refers to a substring of a string of oligo-nucleotides in a sequencing process, for example, DNA or RNA. The fragments may be provided by shearing or fragmenting the string of oligo-nucleotides to obtain a number of substrings that may be named as fragments.

In some implementations, the sequencer 201 may generate some read data, which are the identified oligo-nucleotides, for each fragment of an exemplary string of oligo-nucleotides 203. The sequencer 201 may transmit the read data to the processor 202 for data processing. The data processing may include data analysis and may be done for example, via quality analysis, alignment of read data with a reference genome, assembly of read data, etc. After data processing, depending on the analysis technique, sequencing of some fragments may be stopped because their next oligo-nucleotide bases may include redundant information. A stop command for fragments including redundant data may be sent from the processor 202 to the sequencer 201 to stop the sequencer 201 from sequencing redundant fragments while sequencing of other fragments may continue. The redundant fragments may include fragments which may have a threshold number of the same sequentially identified oligo-nucleotides with at least one other fragment. In exemplary embodiments, the threshold number may be predefined, for example, as a percentage or based on a learning algorithm.

In some implementations, the sequencer 201 may sequence the fragments of the string of oligo-nucleotides by identifying oligo-nucleotides of the fragments one by one using an oligo-nucleotide identification technique. The oligo-nucleotide identification technique may include, for example, analyzing temperature signals, analyzing pH signals, or analyzing fluorescence photons of the oligo-nucleotides.

In some implementations, the processor 202 may process the identified oligo-nucleotides via various processes that may include a data analysis process and a termination process. The data analysis may include analysis of the identified oligo-nucleotides of each fragment to determine the place of the fragment along the string of oligo-nucleotides and to determine the redundant fragments.

In one implementation, the data analysis may be carried out by an analysis process, for example, a quality analysis, alignment to a reference genome or a genome assembly technique. In an exemplary implementation, the data analysis may be done by an alignment process that may include aligning the identified oligo-nucleotides of each fragment to a reference genome to determine the place of the fragment along the reference genome and to determine the redundant fragments.

With further reference to FIG. 2, the termination process may include sending a command to the sequencer 201 to stop the sequencing of the redundant fragments. For example, the termination process may be done by sending a terminating signal from the processor 202 to the sequencer 201 to remove the redundant fragments from further sequencing. The termination process may further include sending a command to the sequencer 201 to stop sequencing process when no informative fragment has any non-identified oligo-nucleotides.

An "informative fragment" as used herein, refers to a fragment that is not a redundant fragment and, therefore, the sequencer should continue its sequencing and identify next oligo-nucleotides within that fragment.

Referring to FIG. 2, in some implementations, the sequencer 201 and the processor 202 may operate in a cycle for each oligo-nucleotide of the fragments after sequencing an initial length of nucleotides by the sequencer 201. The initial length of nucleotides may equal to at least $\log_2 (G)$ initial oligo-nucleotides of each fragment, where G refers to the number of oligo-nucleotides of the under-sequencing string of oligo-nucleotides, for example, the length of a DNA. The initial length of oligo-nucleotides may include a number of at least 30 successively initial nucleotides of each fragment in sequencing a human DNA.

In another aspect, the present disclosure describes a method for sequencing a string of oligo-nucleotides, where a number of under-sequencing strings of oligo-nucleotides may be sheared into a number of fragments. A sequencer may start sequencing each fragment, for example, through determining each oligo-nucleotide type of that fragment sequentially. Subsequently, a processor may analyze the section of that fragment which is sequenced up to that point, for example, by aligning that section of the given fragment to a reference genome. Then, the processor may decide whether the sequencing of that fragment should be further continued or should be stopped at that point. If the processor determines that the sequencing of that fragment should be stopped, that fragment may be detached from the sequencer. Consequently, in further steps of the sequencing, that fragment will not consume any more resources or materials. Benefits from the describe method may include, but are not limited to achieving improvements on the amount of resources or materials used in the sequencing process and/or reducing the time required for an exemplary sequencing process.

Figure 3A:
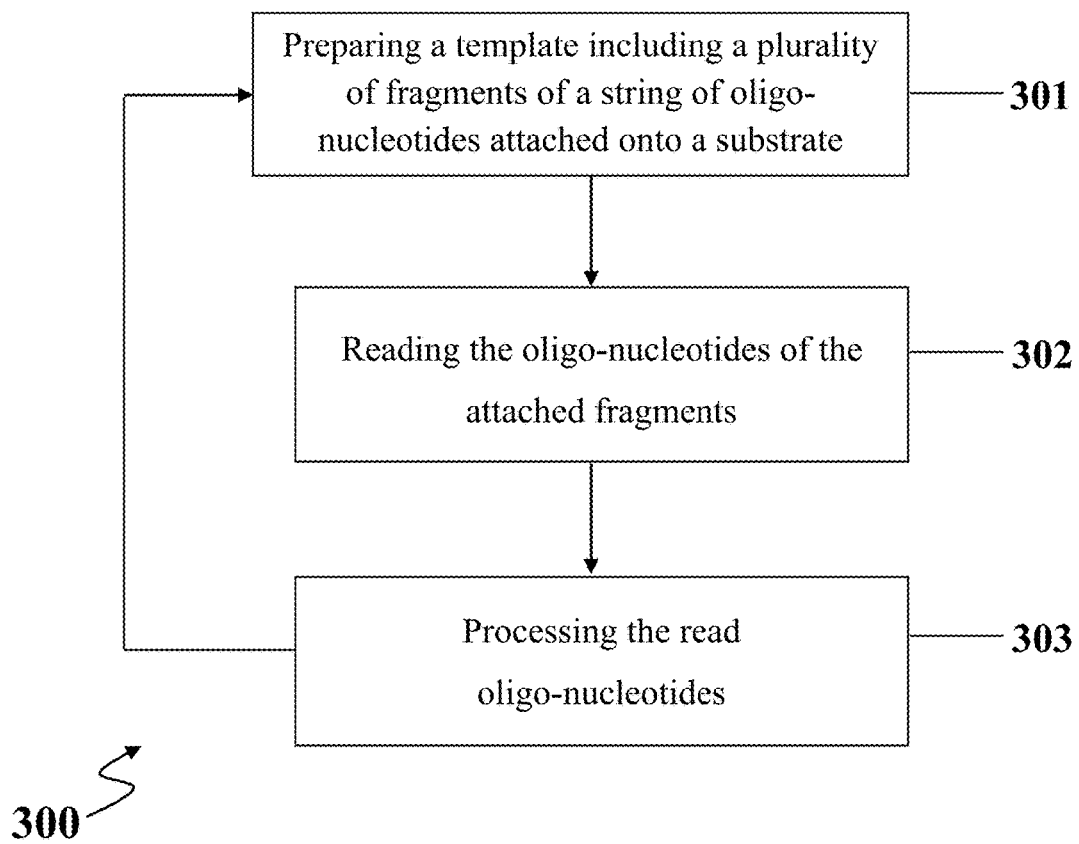
FIG. 3A illustrates a brief flow diagram of an example method for sequencing a string of oligo-nucleotides, according to exemplary implementations of the present disclosure.

FIG. 3A shows an exemplary method 300 for sequencing a string of oligo-nucleotides, according to one or more aspects of the present disclosure. The method 300 may include: preparing a template (step 301); reading the oligo-nucleotides of the attached fragments (step 302); and processing the read oligo-nucleotides (step 303).

In an implementation, the template may include a substrate having a plurality of wells and a plurality of fragments from a string of oligo-nucleotides that may be attached within the wells. The sequencing of oligo-nucleotides along the fragments may be done consecutively and the reading and the processing operations may be done in a cycle for each oligo-nucleotide of the fragments one by one.

The processing of the read oligo-nucleotides (step 303) may include mapping the read oligo-nucleotides along a genome, detecting redundant fragments; and sending a termination signal to stop the reading of the redundant fragments. The redundant fragments may include fragments which may have a threshold number of the same sequentially identified oligo-nucleotides with at least one other fragment.

Figure 3B:
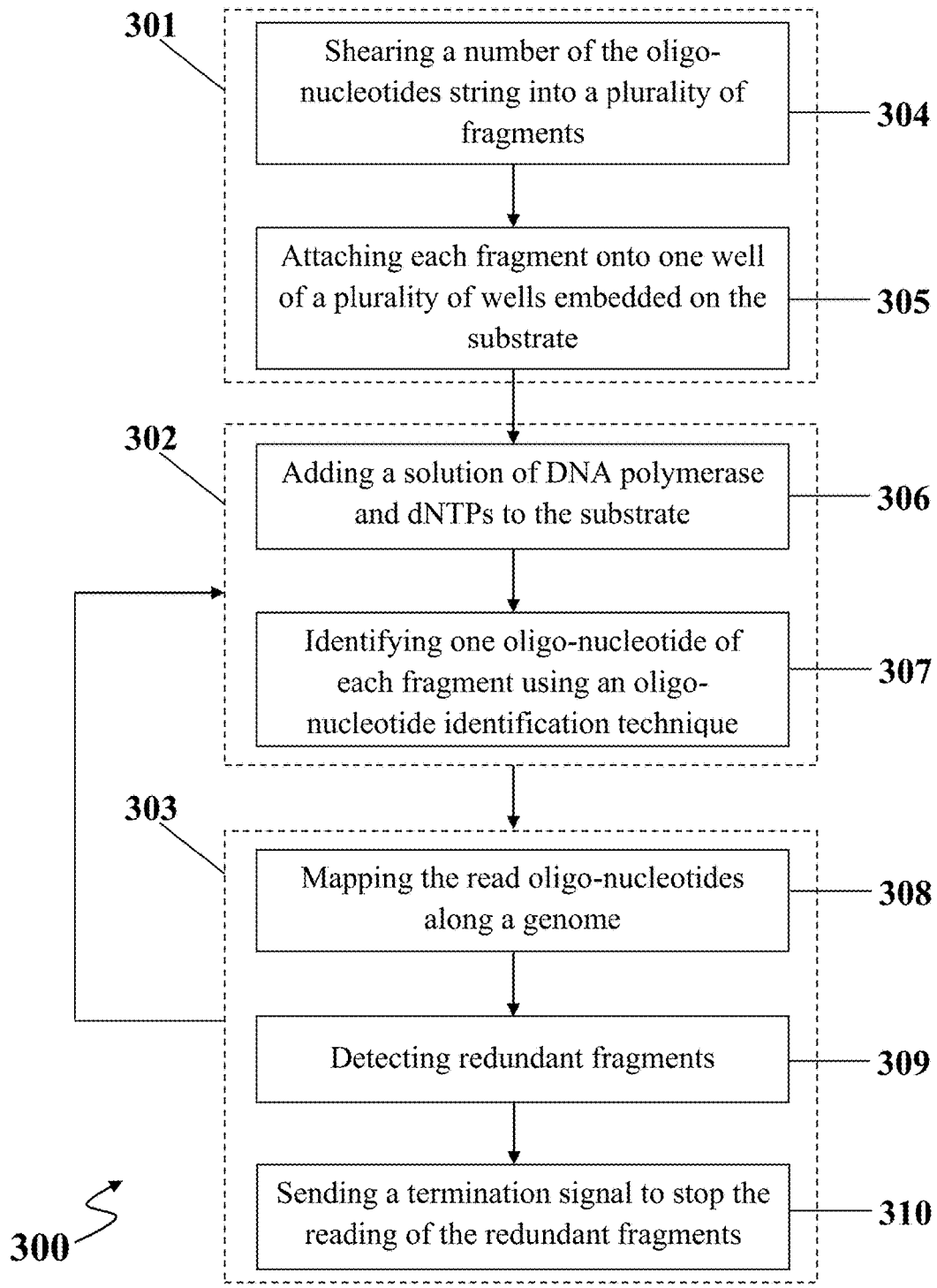
FIG. 3B illustrates an example method for sequencing a string of oligo-nucleotides, according to exemplary implementations of the present disclosure.

FIG. 3B shows an exemplary method 300 for sequencing a string of oligo-nucleotides in more details. In step 301, a template including a plurality of fragments of the string of oligo-nucleotides that may be attached onto a plurality of wells embedded within a substrate may be prepared. The template may be prepared via: shearing a number of the oligo-nucleotides string into a plurality of fragments (step 304); and attaching each fragment onto one well of a plurality of wells embedded on the substrate (step 305).

Moving on to step 302, in the reading process 302, the type of each oligo-nucleotide, for example, types of A, T, C and G may be determined successively along each attached fragment onto the substrate. The reading process 302 may include adding a solution of DNA polymerase and dNTPs to the substrate (step 306); and then, identifying one oligo-nucleotide of each fragment using an oligo-nucleotide identification technique (step 307) which may be the first oligo-nucleotide remained unread along each fragment.

In some implementations, the oligo-nucleotide identification technique may be, for example, analyzing temperature signals, analyzing pH signals, or analyzing fluorescence photons of the oligo-nucleotides. In one exemplary implementation, after each time reading using fluorescence photons of the oligo-nucleotides to identify the oligo-nucleotides, the organic dye or the fluorescent tag may be cleaved and the rest of dNTPs may be washed from the wells after the identifying of the oligo-nucleotides.

Moving on to step 303, the read oligo-nucleotides may be processed to determine their positions along the string of oligo-nucleotides, for example a genome, a DNA, a RNA, etc. The processing of read oligo-nucleotides may be carried out via mapping the read oligo-nucleotides along a genome (step 308); detecting redundant fragments (step 309); and sending a termination signal to stop the reading of the redundant fragments (step 310).

In an implementation, mapping the read oligo-nucleotides along a genome (step 308) may be done using an alignment method to align the read oligo-nucleotides of each fragment to a reference genome. Furthermore, sending the termination signal may include applying a voltage to the bottom of each well including a redundant fragment to detach the redundant fragments from the substrate.

In some implementations, reading the oligo-nucleotides (step 302) and processing of the read oligo-nucleotides (step 303) may be carried out in a cycle for each oligo-nucleotide of the fragments after reading an initial length of nucleotides. The initial length of nucleotides (designated as l) may be equal to a number of the first oligo-nucleotides of each fragment, for example, l=at least $\log_2$ (G), where G refers to the number of oligo-nucleotides of the under-sequencing string of oligo-nucleotides, for example, the length of a DNA. The initial length of oligo-nucleotides may include a number of at least 30 successively initial nucleotides of each fragment in sequencing a human DNA.

In an exemplary implementation, an algorithm is disclosed for processing step 303 to map the read oligo-nucleotides along a genome, for example by aligning the read oligo-nucleotides to a reference genome and to determine the sequence of the string of oligo-nucleotides and to detect a redundant fragment. An example of the algorithm 400 is represented in Table 1.

Referring to Table 1, a number of N read sections of length $L_i$ of a number of N fragments, $\forall i \in \{1, \ldots, N\}$ may be considered. During the processing step 303, the reads that may be obtained from the reading step 302 may be aligned to a reference genome. First, a starting length of the first l bases of all the fragments of a string of oligo-nucleotides, for example, a DNA may be read through the reading operation 302, such that $l=[L_i/K_i]$ for some $K_i$ and $\forall i \in \{1, \ldots, N\}$. The $L=\max_i L_i$ may be denoted as a maximum read length and the set of $R_1=\{R_1(l), \ldots, R_N(l)\}$ may be denoted as the starting l bases of all read fragments. Where, $R_i(l)$ may be the first l bases of the $i^{th}$ fragment. After generating $R_1$, all reads with l bases may be mapped to the reference genome. Some of the reads may be mapped uniquely to the genome; those are named as "anchored". For example, a fragment f may be assumed to be anchored if there is only one location on the reference genome with a Hamming distance no more than $\alpha|f|$, where $|f|$ may be the fragment length (herein, $|f|=l$) and $\alpha$ may be a fixed constant in [0,1] due to the error rate of sequencing reads. The $\alpha$ parameter may be set as the reported error rate of the sequencing method 300.

TABLE 1

An exemplary algorithm 400 for executing the processing of the read oligonucleotides.
Algorithm 400

Input: N fragments with size $L_i$ of a target genome with G bases plus a reference genome with the same length.
Output: A set of reads R, mapped to the reference genome.
Initiate:
Let $L = \max_i L_i$, $R = \emptyset$; and $R^A = \emptyset$. Fix l (the sub-fragment's length), $\alpha \in [0,1]$ and $d = \alpha l$.
Set $R_1$ to be the set of all fragments.
1: for k = 1 to L − l + 1 do
2: if k = 1 then
3: Sequence the first l bases of all the reads in $R_k$.
4: else
5: Sequence the (l + k − 1)-th base of all the reads in $R_k$.
6: end if
7: Map all the reads in $R_k$ to the reference genome, with the last l bases and distance d.
8: Add uniquely mapped reads in $R_k$ to the set $R^A$. Put the rest of reads in the set $R_{k+1}$.
9: Add reads in $R^A$ to R, if by further extensions they will not cover a new base on

TABLE 1-continued

An exemplary algorithm 400 for executing the processing of the read oligonucleotides.
Algorithm 400 thereference genome.
10: Add reads in $R^A$ to $R_{k+1}$, if by further extensions they will cover new bases on thereference genome.
11: end for
12: Align all remaining reads in the $R_{L-l+1}$ the reference genome if any.

Subsequently, After mapping the reads, the set $R_1$ may be partitioned into three disjoint sets of: $R_1^C$, the set of reads that may be anchored to some location on the reference genome whose extension does not increase the coverage; $R_1^A$, the set of reads anchored to somelocation on the genome whose extension will increase the coverage; and $R_1^F$, the set of reads that may not be anchored in the first step. For a read $R_i(l)$ in $R_1^C$, a termination command may be initiated to stop further reading of the $i^{th}$ fragment. The union of $R_1^A$ and $R_1^F$ (i.e. $R_1^A \cup R_1^F$) is denoted by $R_2$ that is the set of fragments on which threading processes will be continued.

Subsequently, the next base of all reads in $R_2$ may be read and the same procedure for mapping and termination may be used. Therefore, this step may end with the set $R_2^C$ of the anchored and terminated reads with length l+1 and the set $R_3$ that may be used for extension in the next step. In this way, one may proceed to step L−l+1, where all the remaining reads may be extended to the maximum read length L. If the set of reads that may be uniquely mapped and terminated in the algorithm be denoted by R, then:

$$R = \cup_{i=1}^{L-l+1} R_i^C$$

Figure 4:
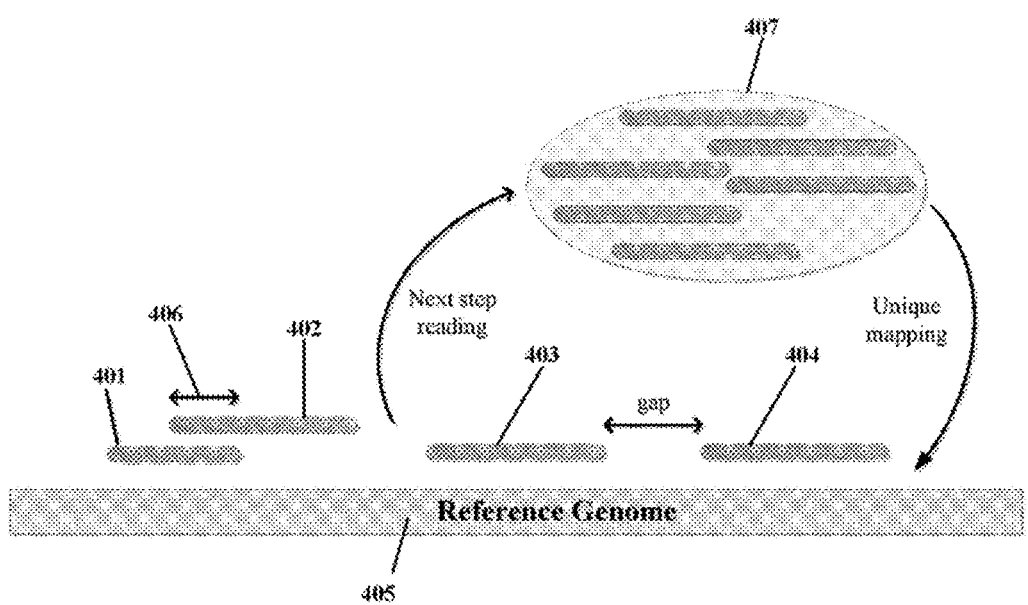
FIG. 4 illustrates a schematic of one example of an algorithm for processing the read oligo-nucleotides using an alignment technique to a reference genome, according to exemplary implementations of the present disclosure.

FIG. 4 shows a schematic representation of the disclosed algorithm 400. Referring to this figure, some anchored reads 401, 402, 403 and 404 are aligned to the reference genome 405. Some anchored reads which their extensions do not specify new bases should be terminated at each step and remove from read set $R_i$ (designated by 407). For example, read 401 which includes some bases that are read more than once (designated by 406) may be terminated and removed from read set $R_i$. Some other anchored reads may be passed to the next step of reading 302 for one base extension (for example, read 403 must be extended). Using this algorithm 400 within method 300, only small fraction of bases are read more than once. Reads in the $R_i$ 407 may be read in the next step of reading the oligo-nucleotides of the attached fragments 302.

Figure 5:
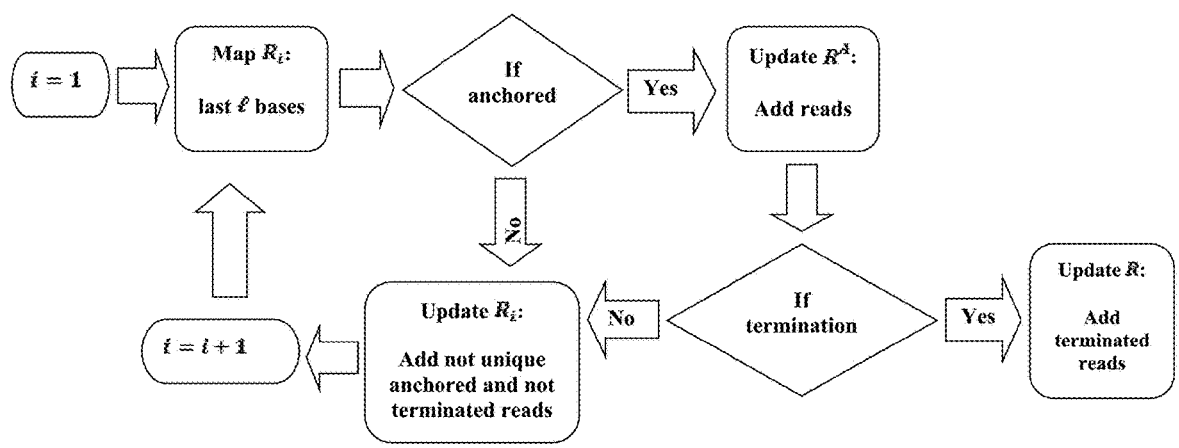
FIG. 5 illustrates an exemplary flow chart of an algorithm for processing the read oligo-nucleotides, according to exemplary implementations of the present disclosure.

Furthermore, FIG. 5 shows an exemplary flow chart of the algorithm 400 for the processing step 303 assisted by using an alignment technique. In each step, the last l bases of all reads in $R_i$ may be mapped to the genome. If some reads are anchored (uniquely mapped to the genome), then these reads may be added to the $R^A$. Then, if extension of any reads in $R^A$ does not cover any new bases, these reads may be terminated in the reading step 302. Otherwise, $R_i$ may be updated by reads in $R^A$ that are not in R (those reads whose extension covers some new bases on the genome that other reads have not covered until this step) and reads that are not anchored. This procedure may continue up to all remaining reads are sequenced or no remaining reads exist within $R_i$.

After detecting the redundant fragments within $R_i$ (step 309), the reading of the redundant fragments may be terminated by sending a termination signal (step 310). Accordingly, an access to each fragment during the reading process 302 may be provided that may provide an addressability and ability to terminate reading the redundant fragments.

In an implementation, a termination signal may send to stop reading the oligo-nucleotides of the redundant fragments. The termination signal may include using an electric field to a well of the substrate that includes a redundant fragment to detach the redundant fragment and consequently, stopping the reading of the redundant fragment. For example, the termination signal may include applying a voltage to the bottom of each well including a redundant fragment to detach the redundant fragments from the substrate that may result to stop the reading of redundant fragments.

Figure 6:
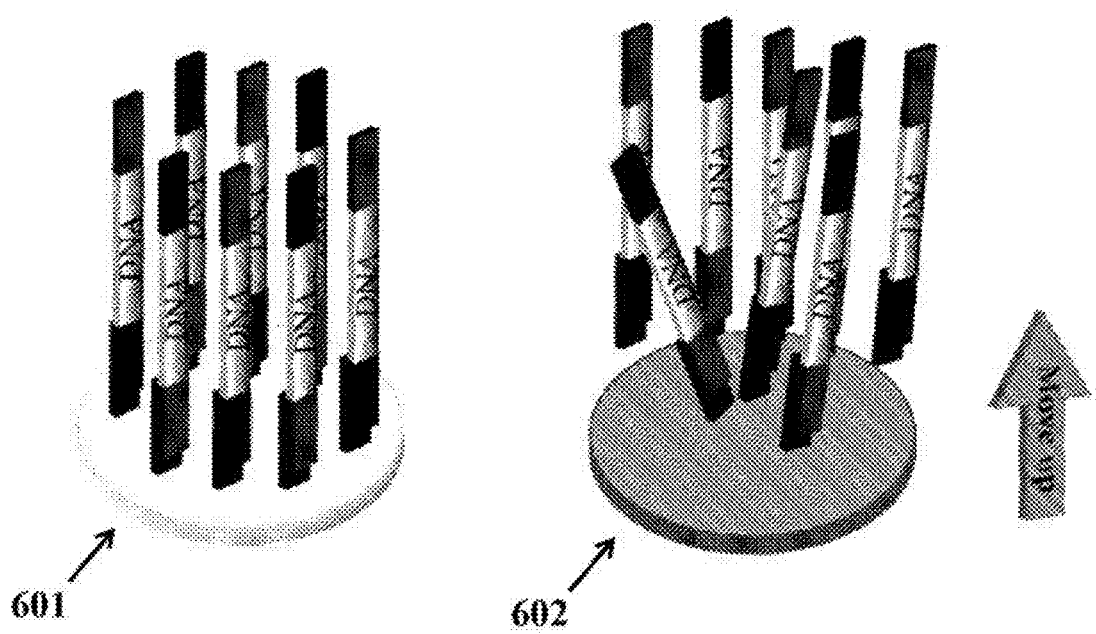
FIG. 6 illustrates a schematic example of the attached fragments onto the substrate (left side) and detaching the fragments from the substrate (right side) during sending a termination signal to a well including redundant fragments, according to exemplary implementations of the present disclosure.

FIG. 6 shows a schematic representation of terminating the reading of a redundant fragment by applying an activation voltage at two input pins at the bottom of wells of a NAND gate. The electric field may force covalent bond between samples and substrate, and after some time the fragments attached to that well may be detached from the substrate. The attached fragments onto the well are shown at the left side of this FIG. 601) and the detachment is at the right side of this FIG. 602).

Figure 7A:
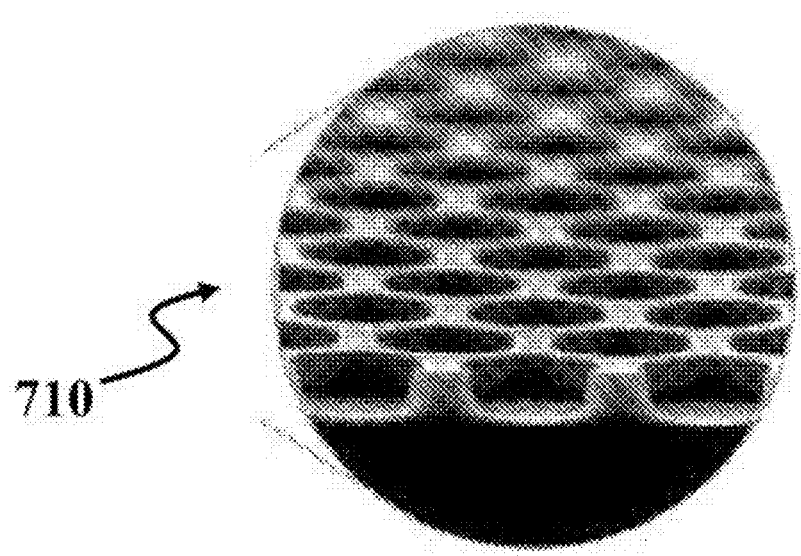
FIG. 7A illustrates an example of a patterned flow cell platform used by Illumina Inc., U.S. used in the present disclosure.

Referring to FIG. 7A, in one implementation, a patterned flow cell platform 710 used by Illumina Inc., U.S. may be supplied to use with some improving design changes as the substrate in step 305 of FIG. 3 that may include a plurality of wells which may be positioned in a grid configuration. Each well may include amplified fragments of the string of oligo-nucleotides. Such platform may be improved to provide an access to the fragments within each well.

Figure 7B:
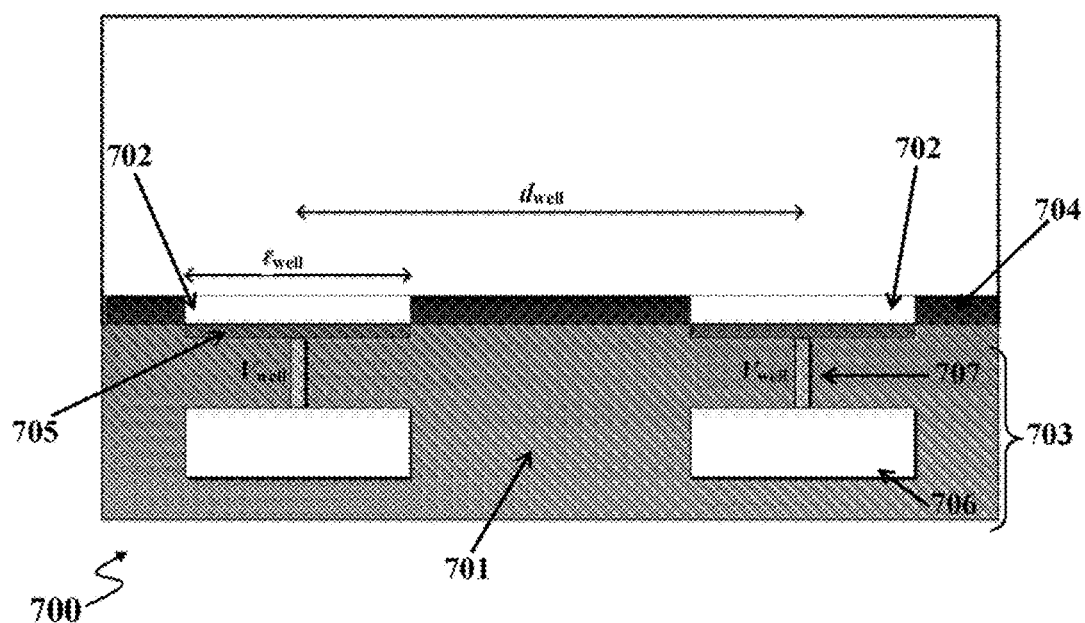
FIG. 7B illustrates an example of a designed improved substrate including a base layer, a plurality of wells embedded on the base layer, and an electrical access to the wells, according to exemplary implementations of the present disclosure.

FIG. 7B shows an example of a designed improved substrate 700, which may include a base layer 701, a plurality of wells 702 embedded on the base layer, and an access 703 to the wells. The base layer may be made of Silicone and may be coated with a metal layer 704. The surface of the wells 702 may be coated with a Gold layer 705. The access 703 may include an electrical circuit at the bottom of each well 702, for example, a NAND logic gate 706 electrically connected to the well 702 by a connecting line 707. The diameter of each well 702 is denoted by $l_{well}$ and the distance between two adjacent wells 702 is denoted by $d_{well}$.

Referring to FIG. 7B, fragments of a string of oligo-nucleotides may defuse in each well 702 and some clusters of the fragments may be formed in wells 702. The electric circuit 703 may be used under each well to establish an access to each well for sending a termination signal if it is needed. Each NAND gate 706 may have two voltage input pins and an output pin that may be electrically connected to the bottom of the well 702. The NAND gate 706 may have a supply voltage rail, for example, about 0V and a ground voltage rail, for example, about −2V. A well located at a location of, for example, (nx, ny) may be selected by applying an activation voltage (for example, about 0V) to the two inputs of the NAND gate 706 associated with that well 702, which may consequently result in a negative output voltage, for example, about −2V. This negative voltage may break the covalent bond between the fragment and the substrate. Thus, all amplified fragments of that well may be detached and may be removed from the solution of DNA polymerase and dNTPs after the detachment of the fragments, which may result to stop reading of those fragments. Therefore, by selecting a well and connecting a negative voltage to the bottom of the well, the connection between thiol/primers/fragments may be broken and these fragments may be detached from the substrate. Continuing the negative voltage connection during the sequencing period may guarantee no oligo-nucleotide entrance to that well.

Figure 7C:
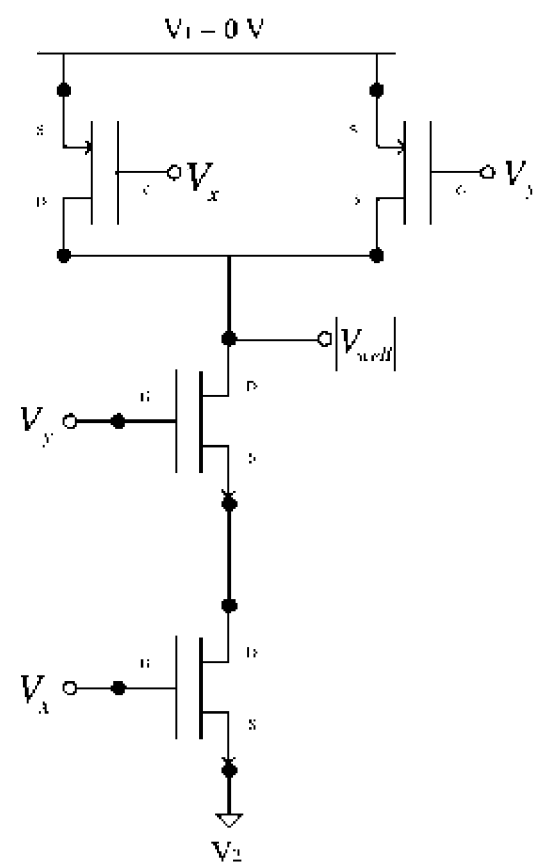
FIG. 7C illustrates an example of an electrical circuit used at the bottom of each well of a substrate for detaching redundant fragments, according to exemplary implementations of the present disclosure.

FIG. 7C shows an exemplary electrical circuit 703 used in the platform of present disclosure under each well 702 for detaching redundant fragments and preventing oligo-nucleotides from entering wells. In this implementation, $V_{well}=V_2$ if $V_x=V_y=0$ and $V_{well}=V_1$, otherwise. For the default mode, where no detachment is considered and all wells are participating in the sequencing process, $V_1=0$ V. In the detachment mode, $V_2$ may be applied at the bottom of some wells. This voltage ($V_2$) should be negative to force the fragments to detach from the substrate. In one example, a value of $V_2=-2$ V may be applied. In addition, $V_x$ and $V_y$ may be controlled by a processor which may receive information from a sequencer as shown in the FIG. 2.

EXAMPLES

Example 1

Human Genome Sequencing

In this example, the algorithm 400 of FIGS. 4 and 5 was simulated for the Human genome hg19. In this simulation, Human genome hg19 was scanned such that from each base an error-less read of length 300 was generated. It was considered that the sub-fragment's length l=30 and distance d=0 or d=1 depends on existing error of sequencing and d=1 was used for alignment distance of the sub-string of length l=30. Also, the Bowtie was used as an aligner. Simulation results are presented in the FIGS. 8 and 9.

Figure 8:
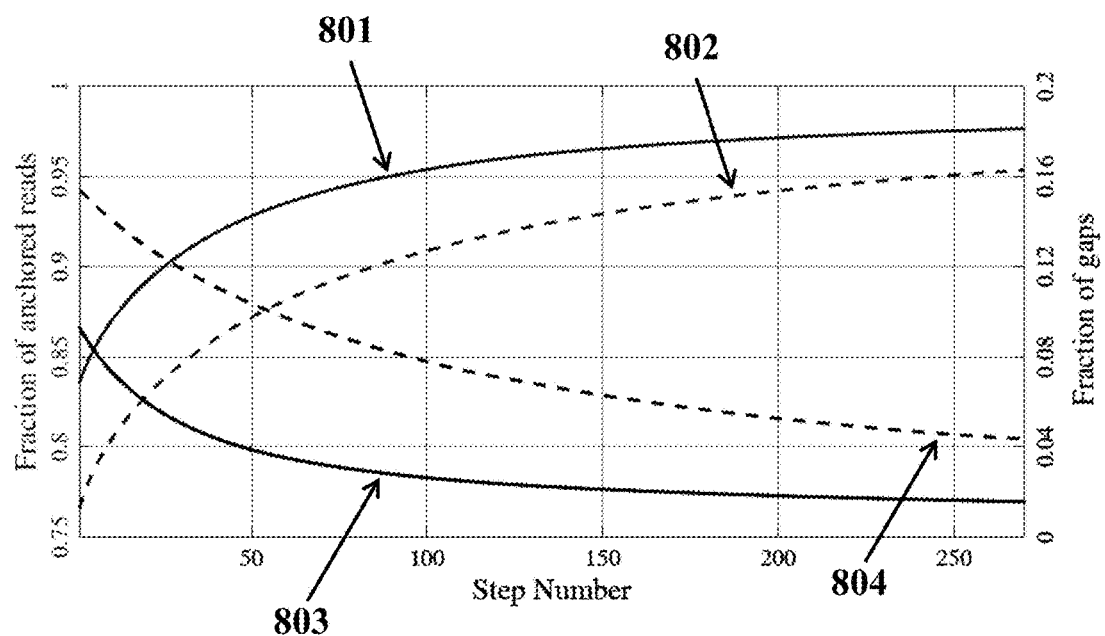
FIG. 8 shows the fraction of anchored reads and the fraction of gap bases within the reference genome as described in more detail in connection with EXAMPLE 1.

FIG. 8 shows the fraction of anchored reads (curves 801 for d=0 and 802 for d=1) at each step of the algorithm 400, from $1^{st}$ step up to $270^{th}$ (=L−l+1-th) step. Also, it shows the fraction of gap bases within the reference genome (curves 803 for d=0 and 804 for d=1) after each step. These results show that a small fraction of the Human genome cannot be uniquely anchored by this method. Almost, about 98% of reads are uniquely anchored to the reference genome with d=0 and less than about 2% of the genome is not covered (gapped bases) by this exemplary algorithm. The distance effect is also illustrated in this figure.

Figure 9:
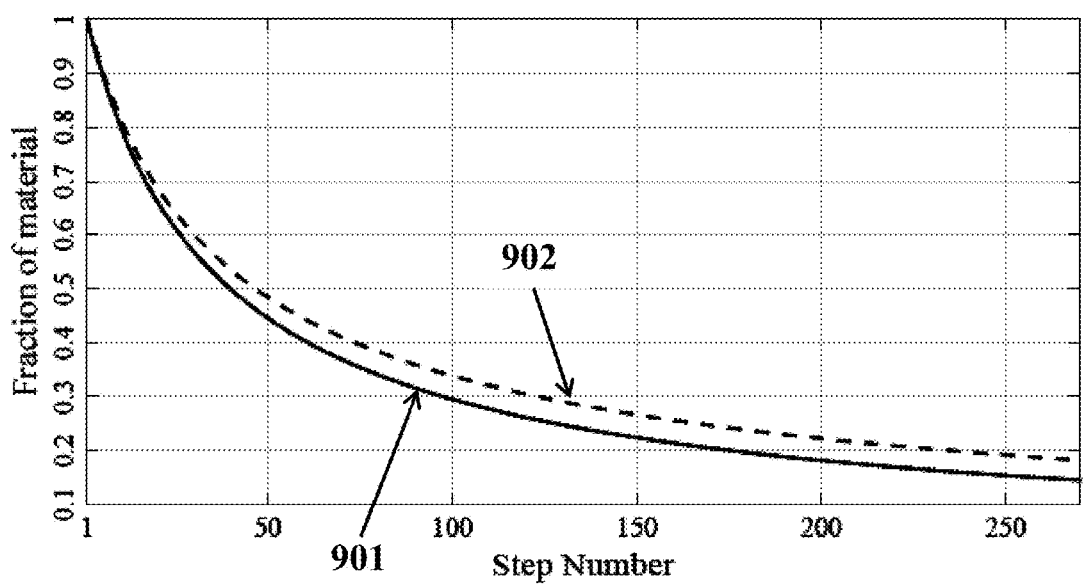
FIG. 9 shows the amount of consumed material in the system and method for sequencing a string of oligo-nucleotides of the present disclosure relative to the amount of consumed material in a classic sequencing system and method as described in more detail in connection with EXAMPLE 1.

In addition, FIG. 9 shows the amount of consumed material in the sequencing system and method of the present disclosure relative to the amount of consumed material in a classic sequencing system and method (e.g. Illumina method) at each step (curve 901 for d=0 and curve 902 for d=1), in which two methods sequence all bases of all reads. The parameters of this simulation are the same as FIG. 8. These simulation results show the strange improvement in the amount of the consumed materials or resources by the proposed algorithm 400 compared with the classic method, such that for read length of L=300 and l=30 (d=0 or d=1), lower than 0.2 (20%) of the materials or resources consumed by the Illumina method is consumed. There exists a trade-off between overall time of sequencing and processing and amount of the consumed materials or resources, such that with the fixed overall time, the amount of the consumed materials or resources may be improved and with the fixed amount of materials, the overall time of sequencing and processing may be improved.

Example 2

Voltage Analysis

To determine the necessary value of negative voltage ($V_{well}$), the system and method of the present disclosure as shown in FIGS. 7B and 7C was simulated with an ionized solution to find the electric field within each well and near the adjacent wells.

Figure 10A:
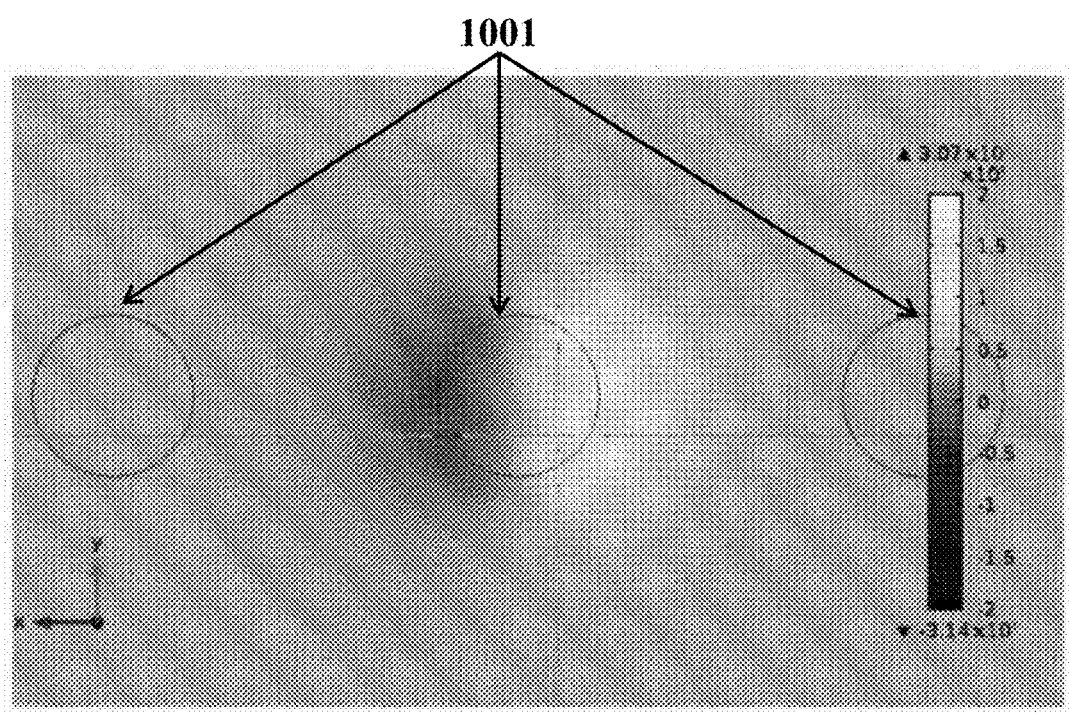
FIG. 10A shows the magnitude of the electric field in the x-axis ($E_x$) when the $V_{well}$=−2 V is applied to the center of well, $l_{well}$=1 μm and $l_{well}$=1.5 μm as described in more detail in connection with EXAMPLE 2.
Figure 10B:
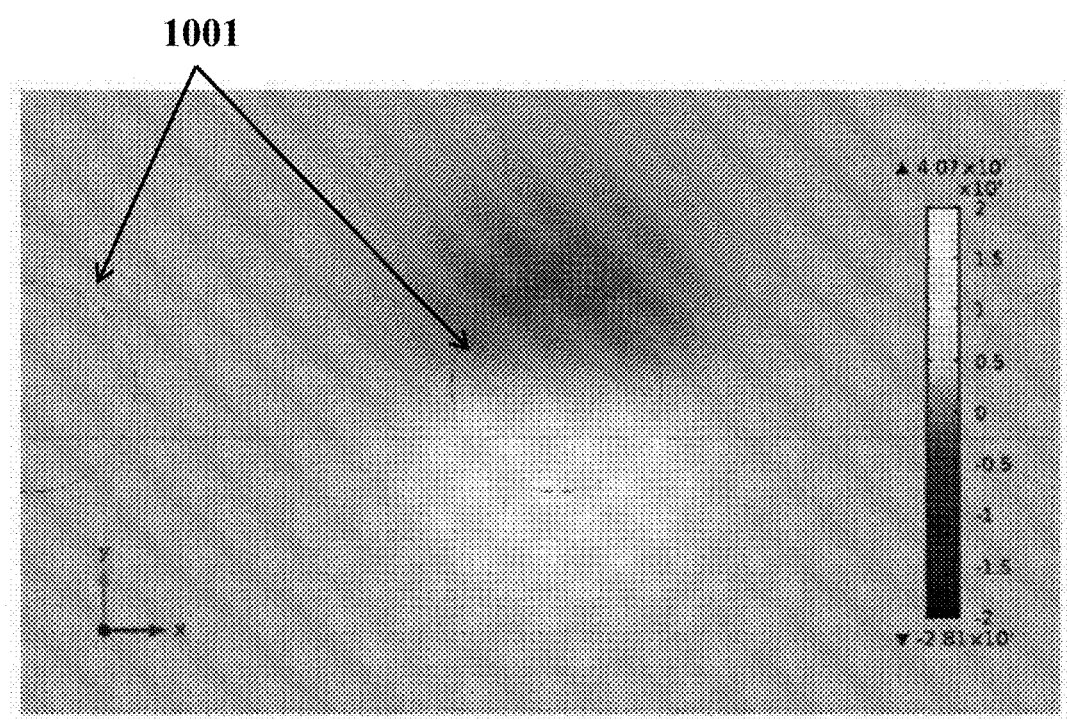
FIG. 10B shows the magnitude of the electric field in the y-axis ($E_y$) when the $V_{well}$=−2 V is applied to the center of well, $l_{well}$=1 μm and $l_{well}$=1.5 μm as described in more detail in connection with EXAMPLE 2.

FIG. 10A shows the magnitude of the electric field in the x-axis ($E_x$) when the $V_{well}=-2$ V is applied to the center of well, $l_{well}=1$ μm and $d_{well}=1.5$ μm. FIG. 10B shows the magnitude of the electric field in the y-axis ($E_y$) when a $V_{well}$ of about −2 V is applied to the center of well, $l_{well}=1$ μm and $d_{well}=1.5$ μm. The magnitudes of these electric fields are in an order of about $10^4$ V/m near the edges of the well while the magnitudes of these electric fields are in an order of about $10^5$ V/m at the center of well. Exemplary wells are represented by 1001 in FIGS. 10A and 10B.

Figure 11A:
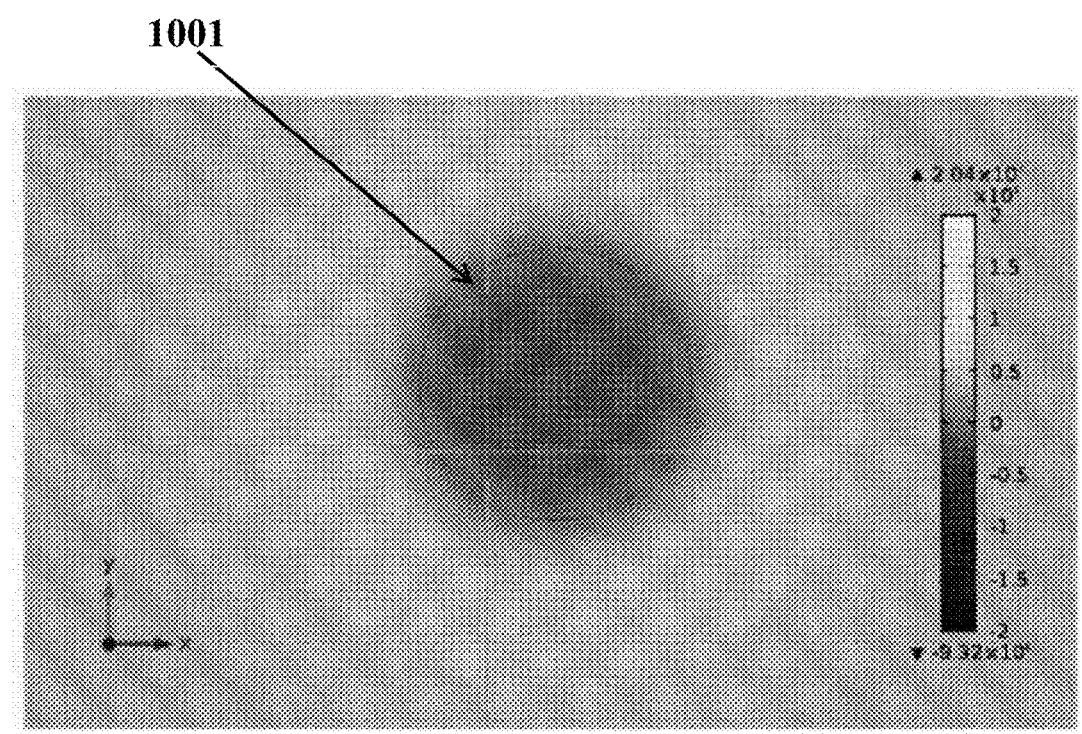
FIG. 11A shows a top z-axis view of the magnitude of the electric field in the z-axis ($E_z$) when the $V_{well}$=−2 V is applied to the center of well, $l_{well}$=1 μm and $l_{well}$=1.5 μm as described in more detail in connection with EXAMPLE 2.
Figure 11B:
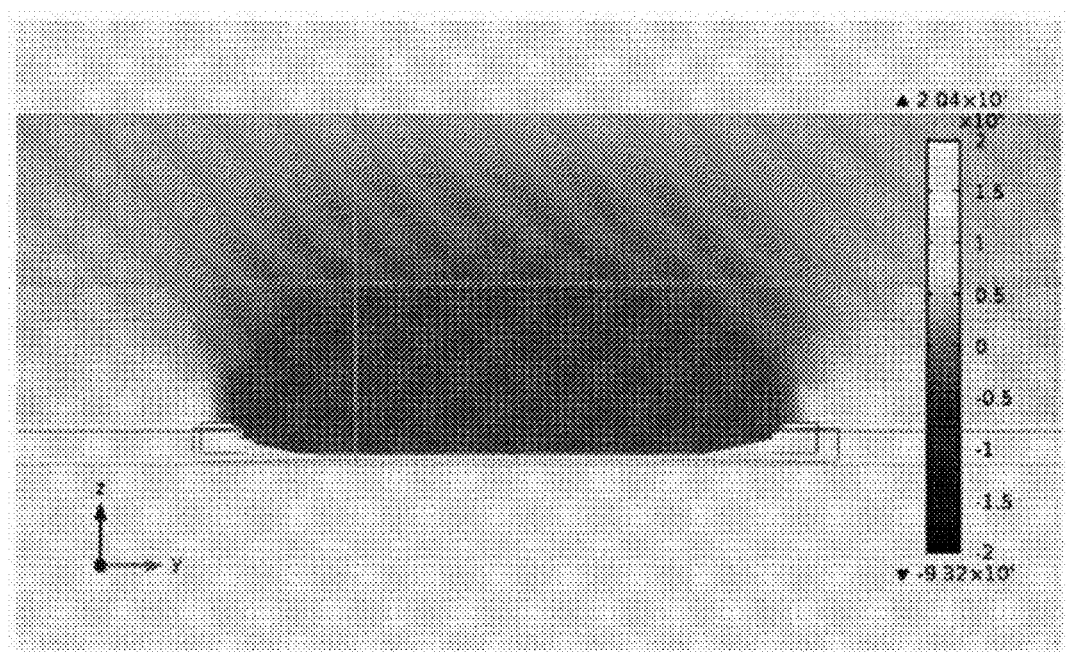
FIG. 11B shows a cross section z-axis view of the magnitude of the electric field in the z-axis ($E_z$) when the $V_{well}$=−2 V is applied to the center of well $l_{well}$=1 μm and $l_{well}$=1.5 μm as described in more detail in connection with EXAMPLE 2.

FIGS. 11A and 11B shows the magnitude of the electric field in the z-axis ($E_z$) when a $V_{well}$ of about −2 V is applied to the center of well 1001, $l_{well}=1$ μm and $d_{well}=1.5$ μm from a top view (FIG. 11A) and from a cross section view (FIG. 11B). The magnitude of this electric field is in the order of about $2\times10^4$ V/m near the edges of the well 1001 while the magnitude of this electric filed is in the order of about $2\times10^6$ V/m at the center of the well 1001.

This simulation shows that the electric force may change an order of magnitude in vicinity of the wells. Also, the electric force of the detached wells facilitates diffusion of oligo-nucleotides to adjacent wells, improving the diffusion time. Thus, an appropriate value for negative voltage should be set to prevent oligo-nucleotides from entering the detached wells while not disturbing other nucleotides. So, a value of about $V_{well}$=about −2 V may be proposed.

Example 3

Circuit Analysis

A grid structure for wells of the flow cell platform may be considered in the two directions of x and y. To select each well, it may be considered the NAND gates are below of each well and $V_{well}$=about −2 V in an active mode. An example of this circuit is presented in FIG. 7C. Initially, all voltages may be set to zero. To select each well, the corresponding x- and y-axis voltages may be changed to about −2 V. For implementing this circuit, almost $50L_t$ of area may be needed below each well, where $L_t$ is the length of a CMOS transistor. The state-of-the-art technology may be $L_t \approx 20$ nm; thus, $50L_t \approx 1$ μm. As, $d_{well} \geq 50L_t$, for this technology $d_{well} \approx 1$ μm.

In addition, for DNA amplification, for example, Illumina's, a value of $l_{well}$ in a range of about $l_{well}=0.5$ μm to about $l_{well}=1$ μm may be an appropriate value. As mentioned in voltage analysis (EXAMPLE 2 hereinabove), the electric field simulations may justify that $d_{well} \geq 1.5\ l_{well}$ may be an appropriate value for distance of adjacent wells.

Example 4

Two-Phase Read Generation

In this example, sequencing of a human genome by a two-phase read generation is demonstrated. For this purpose, DNA fragments from an individual may be immobilized to a surface. The sequencing may be performed in two phases. The first l=40 bases of all fragments may be read by the sequencer and the resulting reads may be fed to the processor. Reads that can be mapped uniquely and their extension do not add information may be detected by the processor and their corresponding fragments may be detached from the surface at the sequencer using the provided system and method. The rest of fragments may be sequenced to maximum length.

Example 5

Paired-End Sequencing

In this example, sequencing of a human genome is demonstrated by a paired-end sequencing. For this purpose, DNA fragments from an individual may be immobilized to a surface. The sequencing may be performed in two phases. The first l=40 bases of all fragments may be read by the sequencer and the resulting reads may be fed to the processor. Reads that may be mapped uniquely and their pairs do not add information may be detected by the processor and their corresponding fragments may be detached from the surface at the sequencer using the provided system and method. The other end of remaining fragments may be sequenced with L=40.

Example 6

Variation Detection

In this example, detecting of variation detection in a human genome is demonstrated. For this purpose, DNA fragments from an individual may be immobilized to a surface. The first l=40 bases of all fragments may be read by the sequencer and the resulting reads may be fed to the processor. The processor may align the reads to a reference genome and may compute the likelihood of variation at any locus on the reference genome. Loci with high confident level of variation may be detected and the DNA fragments related to those loci may be detected by the processor. The extra fragments may be detached from the surface by the provided system and method. The sequencing may be continued until the confident level of each locus is above some threshold.

Example 7

Targeted Sequencing

In this example, targeted sequencing of a human genome is demonstrated. In many applications, it may only be needed to sequence targeted loci on a genome. For this purpose, the DNA fragments from an individual may be immobilized to a surface and a first l=30 bases may be read by the sequencer. Reads that are not related to the targeted loci may be detected by mapping reads to the reference genome by the processor. The corresponding fragments may be detached from the surface as described in the provided system and method. The rest of fragments may be sequenced up to the maximum length that can be sequenced by the sequencer.

What is claimed is:

1. A method for sequencing a string of oligo-nucleotides, comprising:
  preparing a template, the template comprising:
    a substrate having a plurality of wells; and
    a plurality of fragments from a string of oligo-nucleotides attached within the wells,
  reading the oligo-nucleotides of the attached fragments; and
  processing the read oligo-nucleotides, comprising:
    mapping the read oligo-nucleotides along a genome using an alignment method to align the read oligo-nucleotides of each fragment to a reference genome;
    detecting redundant fragments; and
    sending a termination signal to stop the reading of the redundant fragments responsive to detecting the redundant fragments,
  wherein:
    the reading and the processing operations are done in a cycle for each oligo-nucleotide of the fragments; and
    the redundant fragments include fragments having a threshold number of the same sequentially read oligo-nucleotides with at least one other fragment.

2. The method of claim 1, where the threshold number is predetermined.

3. An integrated system for sequencing a string of oligo-nucleotides, comprising:
  a sequencer, configured to sequence a plurality of fragments of the string of oligo-nucleotides via identifying oligo-nucleotides of the fragments one by one; and
  a processor, configured to:
  process the identified oligo-nucleotides to determine the sequence of the string of oligo-nucleotides;
  detect redundant fragments; and
  stop the sequencer from sequencing redundant fragments responsive to detection of redundant fragments,
  wherein the sequencer and the processor operate in a cycle for each oligo-nucleotide of the fragments.

4. The system according to claim 3, wherein the oligo-nucleotides are identified by using an identification technique that is selected from the group consisting of analyzing temperature signals, analyzing pH signals, or analyzing fluorescence photons of the oligo-nucleotides.

5. The system according to claim 3, wherein the redundant fragments comprise fragments having a threshold number of the same sequentially identified oligo-nucleotides with at least one other fragment.

6. The system according to claim 3, wherein the process of the identified oligo-nucleotides comprises:
  analyzing the identified oligo-nucleotides of each fragment to determine the place of the fragment along the string of oligo-nucleotides and to determine the redundant fragments; and
  sending a command to the sequencer to stop the sequencing of the redundant fragments.

7. The system according to claim 6, wherein analyzing the identified oligo-nucleotides of each fragment is done by an analysis process that is selected from a group consisting of quality analysis, alignment and genome assembly technique.

8. The system according to claim 7, wherein analyzing the identified oligo-nucleotides of each fragment is done by an alignment method, including aligning identified oligo-nucleotides of each fragment to a reference genome to determine the place of the fragment along the reference genome and to determine the redundant fragments.

9. The system according to claim 6, wherein sending a command to the sequencer to stop the sequencing of the redundant fragments includes sending a terminating signal from the processor to the sequencer to remove or stop the redundant fragments from further sequencing.

10. A method for sequencing a string of oligo-nucleotides, comprising:
   preparing a template, the template comprising:
      a substrate having a plurality of wells; and
      a plurality of fragments from a string of oligo-nucleotides attached within the wells,
   reading the oligo-nucleotides of the attached fragments; and
   processing the read oligo-nucleotides, comprising:
      mapping the read oligo-nucleotides along a genome;
      detecting redundant fragments; and
      sending a termination signal to stop the reading of the redundant fragments responsive to detecting redundant fragments,
   wherein the reading and the processing operations are done in a cycle for each oligo-nucleotide of the fragments.

11. The method according to claim 10, wherein the redundant fragments include fragments having a threshold number of the same sequentially read oligo-nucleotides with at least one other fragment.

12. The method according to claim 10, wherein the preparing the template comprises:
   shearing a number of the oligo-nucleotides string into a plurality of fragments; and
   attaching each fragment onto one well of a plurality of wells embedded on the substrate.

13. The method according to claim 10, wherein the reading the oligo-nucleotides of the fragments comprises:
   adding a solution of DNA polymerase and dNTPs to the substrate; and
   identifying one oligo-nucleotide of each fragment using a nucleotide identification technique.

14. The method according to claim 13, wherein the nucleotide identification technique is selected from the group consisting of analyzing temperature signals, analyzing pH signals, or analyzing fluorescence photons of the oligo-nucleotides.

15. The method according to claim 10, wherein the mapping the read oligo-nucleotides along a genome is done assisted by an alignment method to align the read oligo-nucleotides of each fragment to a reference genome.

16. The method according to claim 10, wherein the substrate comprises:
   a base layer,
   a plurality of wells fabricated on the base layer; and
   an access to the wells.

17. The method according to claim 16, wherein the access comprises an electrical circuit at the bottom of each well.

18. The method according to claim 16, wherein the access comprises a NAND logic gate electrically connected to a well by an electrical connector.

19. The method according to claim 10, wherein the sending the termination signal includes applying a voltage to the bottom of each wells including a redundant fragment to detach the redundant fragments from the substrate.

* * * * *